(12) United States Patent
Veera Reddy et al.

(10) Patent No.: US 7,923,566 B2
(45) Date of Patent: Apr. 12, 2011

(54) ALTERNATIVE PROCESS FOR THE PREPARATION OF LOSARTAN

(75) Inventors: Arava Veera Reddy, Hyderabad (IN); Siripalli Udaya Bhaskara Rao, Hyderabad (IN); Chinnapillai Rajendiran, Hyderabad (IN); Venkateswarlu Jasti, Hyderabad (IN)

(73) Assignee: Suven Life Sciences Limited, Hyderabad (IN)

( * ) Notice: Subject to any disclaimer, the term of this patent is extended or adjusted under 35 U.S.C. 154(b) by 57 days.

(21) Appl. No.: 11/990,456

(22) PCT Filed: Dec. 21, 2005

(86) PCT No.: PCT/IN2005/000426
§ 371 (c)(1),
(2), (4) Date: Feb. 14, 2008

(87) PCT Pub. No.: WO2007/020654
PCT Pub. Date: Feb. 22, 2007

(65) Prior Publication Data
US 2010/0190996 A1    Jul. 29, 2010

(30) Foreign Application Priority Data
Aug. 16, 2005   (IN) .......................... 1133/CHE/2005

(51) Int. Cl.
  *C07D 403/10*  (2006.01)
  *C07D 257/00*  (2006.01)
  *C07F 5/06*    (2006.01)
(52) U.S. Cl. ...................................... 548/250; 548/252
(58) Field of Classification Search .................. 548/250, 548/252, 254
See application file for complete search history.

(56) References Cited

U.S. PATENT DOCUMENTS

| | | | |
|---|---|---|---|
| 5,484,995 A | 1/1996 | Scofield et al. | |
| 6,774,241 B2 | 8/2004 | Clark et al. | |
| 2010/0222597 A1* | 9/2010 | Veera Reddy | 548/252 |

FOREIGN PATENT DOCUMENTS

| | | |
|---|---|---|
| EP | 0578125 A | 1/1994 |
| WO | WO-9827081 A1 | 6/1998 |
| WO | WO-9902502 A2 | 1/1999 |
| WO | WO-9937623 A2 | 7/1999 |
| WO | WO-9942465 A2 | 8/1999 |
| WO | WO-0132646 A2 | 5/2001 |
| WO | WO-02098878 A1 | 12/2002 |
| WO | WO-03065046 A2 | 8/2003 |
| WO | WO-03066056 A1 | 8/2003 |
| WO | WO-03072548 A1 | 9/2003 |
| WO | WO-2004035047 A1 | 4/2004 |
| WO | WO-2004048328 A2 | 6/2004 |
| WO | WO-2004048330 A1 | 6/2004 |
| WO | WO-2004048331 A1 | 6/2004 |
| WO | WO-2004055026 A1 | 7/2004 |
| WO | WO 2005/014602 * | 2/2005 |
| WO | WO-2005014602 A | 2/2005 |

OTHER PUBLICATIONS

Monsma, F. J., Jr. et al, "Cloning and Expression of a Novel . . . ", Molecular Pharmacology, 1993, 43, 320-327, Am Society for Pharm and Experimental Therapeutics, USA.
Kohen, R. et al, "Cloning, Characterization, and Chromosomal . . . ", Journal of Neurochemistry, 1996, 66, 47-56, Lippincott-Raven Publishers, USA.
Ruat, M. et al, "A Novel Rat Serotonin (5-HT6) Receptor . . . ", Biochemical Biophysical Research Communications, 1993, 193, 268-276, Academic Press.
Ward, R. P. et al, "Localization of Serotonin Subtype 6 Receptor . . . ", Neuroscience, 1995, 64, 1105-1111, Elsevier Science Ltd, UK.
Reavill, C. et al, "The Therapeutic Potential of 5-HT6 . . . ", Current Opinion in Invesigational Drugs, 2001, 2(1):104-109, PharmaPress Ltd.
Gerard, C. et al, "Immuno-localization of serotonin 5-HT6 receptor-like material . . . ", Brain Research, 1997, 746, 207-219, ,Elsevier Science B.V.
Bentley, J. C. et al, "Investigation of stretching behaviour induced by the selective . . . ", British Journal of Pharmacology, 1999, 126 (7), 1537-1542, Stockton Press.
Dawson, L. A. et al, "In vivo effects of the 5-HT6 antagonist . . . ", British Journal of Pharmacology, 2000, 130 (1), 23-26, Macmillan Publishers Ltd.
Rogers, D. C. et al, "The Selective 5HT6 Receptor Antagonist", Society of Neuroscience, Abstracts, 2000, 26, 680, UK.
Ernst, M. et al, "DOPA Decarboxylase Activity in Attention Deficit . . . ", Journal of Neuroscience, 1998, 18(15), 5901-5907, Society for Neuroscience, USA.
Branchek, T. A. et al, Annual Reviews in Pharmacology and Toxicology, 2000, 40, 319-334, Annual Reviews, USA.
Stean, T. et al, "Anticonvulsant Properties of the Selective 5-HT6 Receptor . . ." British Journal of Pharmacology, 1999, 127 Proc. Supplement-131P.
Routledge, C., "Characterization of SB-271046: A Potent . . . ", British Journal of Pharamacology, 2000, 130, 1606-1612, Macmillan Publishers Ltd.
Roth, B.L. et al., "Binding of Typical and Atypical Agents . . . ", Journ of Pharm and Experimental Therapeutics, 1994, 268, pp. 1403-1410, Am Society for Pharm and Exp. Ther. Wooley, M.L. et al., "A Role for 5-HT6 Receptors in Retention of Spatial Learning . . . ", Neuropharmacology, 2001, 41: 210-219, Elsevier Science Ltd.
Berge, Stephen et al., "Pharmaceutical Salts", Journal of Pharmaceutical Sciences, 1977, 66, 1-19.
Kask, A. et al., "Neuropeptide Y Y5 Receptor Antagonist CGP71683A . . . ", European Journal of Pharmacology, 414, 2001, 215-224, Elsevier Science B.V.
Turnbull, A. et. al., "Selective Antagonism of the NPY Y5 Receptor Does Not . . . ", Diabetes, 51, 2002, 2441-2449.
Ennaceur, A. et al, "A New One-trial Test for Neurobiological Studies of Memory . . . ", Behavioural Brain Research, 1988, 31, 47-59, Elsevier Science Publishers.

(Continued)

Primary Examiner — Susannah Chung
(74) Attorney, Agent, or Firm — IpHorgan Ltd

(57) ABSTRACT

The invention relates to an improved process for the preparation of Losartan. The process comprising reacting 2-n-butyl-4-chloro-5-formyl imidazole with 2-(4-bromomethyl) benzonitrile in the presence of a phase transfer catalyst and an alkali, and reducing the resulting cyano aldehyde to produce a cyano alcohol which is further reacted with sodium azide in N-methyl pyrrolidinone and a salt to produce Losartan.

18 Claims, No Drawings

OTHER PUBLICATIONS

King, M. V. et. al., "5-HT6 Receptor Antagonists Reverse Delay-dependent . . . ", Neuropharmacology, 2004, 47, 195-204, Elsevier Ltd.

Yamada, N. et al., "Improvement of Scopolamine-induced Memory Impairment . . .", Pharmacology, Biochem. And Behaviour, 2004, 78, 787-791, Elsevier Inc.

Linder, M. D. et al., "An Assessment of the Effects of Serotonin 6 . . . ", Journal of Pharm and Exp. Ther., 2003, 307 (2), 682-691, Am Soc. for Pharm and Exp. Ther., USA.

Callahan, P. M. et al., "Characterization of the Selective 5-HT6 Receptor . . . ", Abstract, 776.19.2004, Society for Neuroscience, 2004.

Fox, G. B. et al., "Memory Consolidation Induces a Transient and . . . ", Journal of Neurochemistry, 1995, 65, 6, 2796-2799, Lippincott-Raven Publishers, USA.

Carini, D.J. et al., Nonpeptide Angiotensin II Receptor Antagonists . . . :, Journal of Medicinal Chemistry, 1991, 34, 2525-2547, American Chemical Society, USA.

* cited by examiner

ALTERNATIVE PROCESS FOR THE PREPARATION OF LOSARTAN

The invention disclosed in this application relates to an improved process for the preparation of Losartan. Losartan and its potassium salt, having the formulae (1) & (2) respectively are angiotensin-II receptor (Type AT1) antagonists.

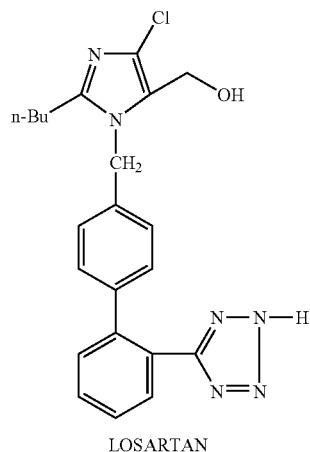

LOSARTAN

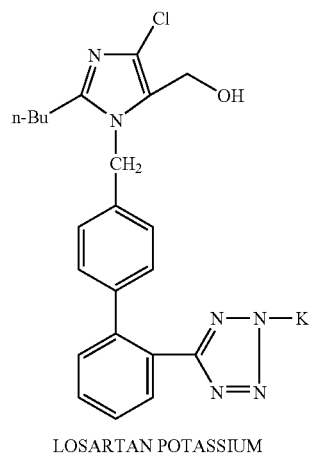

LOSARTAN POTASSIUM

In adults Losartan is currently indicated for the treatment of hypertension. (in hypertensive patients with left ventricular hypertrophy, it is also indicated to reduce the risk of stroke).

BACKGROUND

Losartan Potassium having the formula (2) and its principle active metabolite block the vasoconstrictor and aldosterone. Secreting effects of angiotensin II by selectively blocking the binding of angiotensin II to the AT1 receptor found in many tissues (e.g., vasicular smooth muscle, adrenal gland) otherwise called as angitensin receptor blockers (ARBs).

PRIOR ART

There are many processes recorded in literature. The latest prior art information for the preparation of Losartan is the disclosure made in the patent application of Novartis in their PCT WO 2005/014602 dated 17 Feb. 2005.

The process described in the application comprises the reaction of 4'-(Bromomethyl)-2-cyanobiphenyl (Bromo OTBN) of the formula (3) with 2-n-butyl-4-chloro-5-formyl imidazole (BCFI) of the formula (4) in the presence of Potassium carbonate and acetonitrile to give cyano aldehyde of the formula (5). The Cyano aldehyde of the formula (5) is reduced with sodium borohydride to get cyano alcohol of the formula (6). The Cyano alcohol is reacted with diethyl aluminium azide in the presence of triethyl aluminium to give Losartan of the formula (1).

The reaction scheme of the process is shown in the Scheme 1

Scheme 1

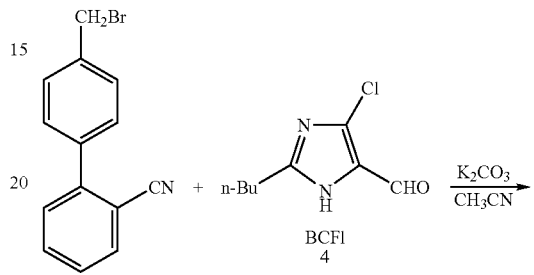

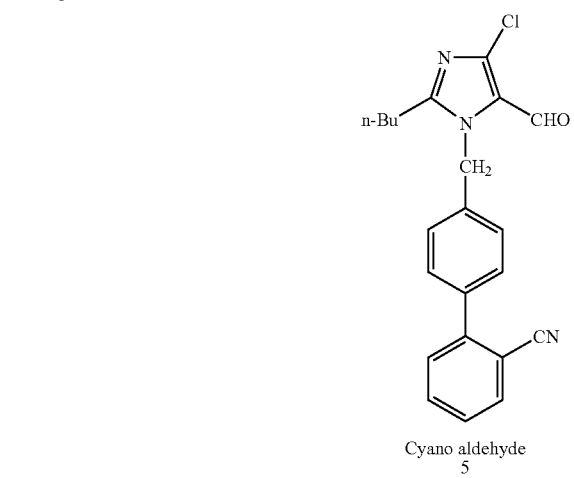

Cyano aldehyde
5

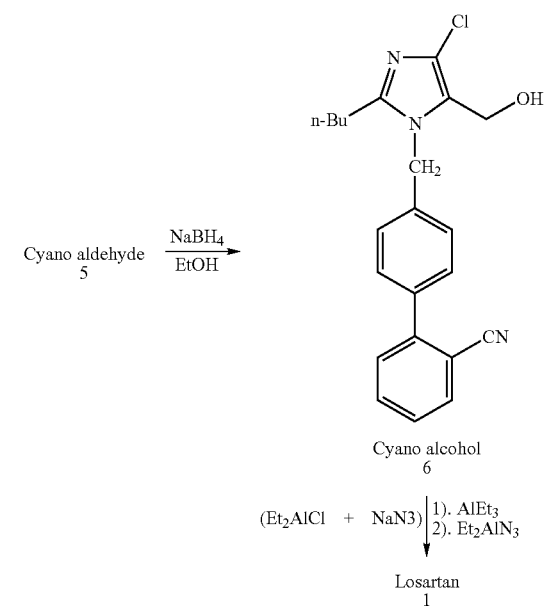

Even though the process is simple, handling of triethyl aluminium used needs special attention like very anhydrous conditions, reactions are to be performed under nitrogen or argon and transferring of triethyl aluminium from the containers needs anhydrous systems. The neat liquid and dense solutions of triethyl aluminium are known to ignite very easily at room temperature in presence of air. (Pyrophoric). So handling of both triethyl aluminium and diethyl aluminium needs special attention like anhydrous conditions, nitrogen atmosphere etc.

In EP 0578125A1 of Takeda Chemical Industries dated 12 Jan. 1994, yet another method for the preparation of Losartan has been disclosed in which Trioctadecyl or Trioctyl tin azide has been used as a tetrazole-forming agent. This method also uses the Cyano alcohol of the formula (6). The process comprises reacting the cyano alcohol of the formula (6) with tri-n-octyl tin azide in presence of toluene to give tri-n-octyl tetrazole derivative which was treated with nitrous acid to give Losartan of the formula (1) in 94.7% yield.

The reaction scheme of the process is shown in the Scheme 2

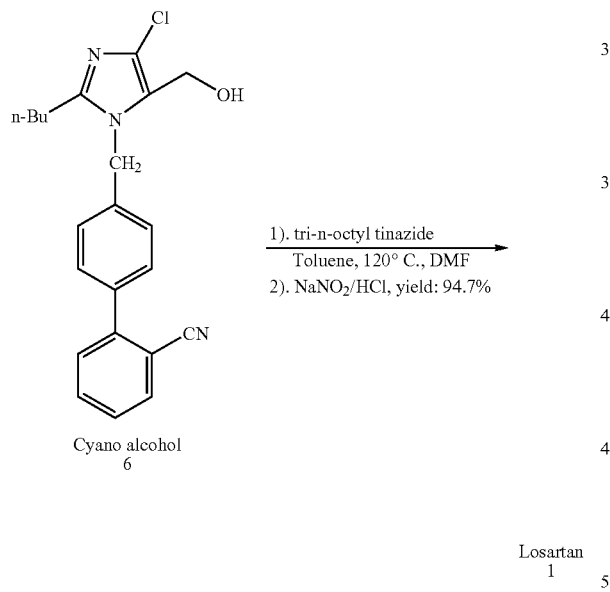

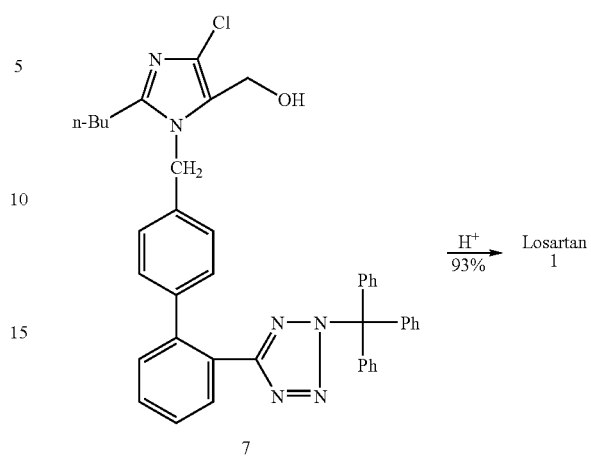

Even though the yields are better (94.7%) in this process again handling of tri-n-octyl tin azide is involved and tin (as heavy metal) contaminants in the chug has to be monitored as per pharmacopoeial methods.

Dupont/Merck in their patents and papers always described that trityl losartan of the formula (7) is detritylated to get Losartan. They have used trimethyl tin azide or tri alkyl tin azides for the preparation of tetrazoles. The trityl Losartan of the formula (7) is reacted with mineral acid to give Losartan of the formula (1). The trityl Losartan of the formula (7) is prepared using trimethyl or trialkyl tin azide for the formation of tetrazole nucleus.

The reaction scheme of the process is shown in the Scheme 3

For example they described in J. Med. Chem. 1991, 34, 2525-2547, the preparation of compound of the formula 7 as follows.

The Cyano alcohol of the formula (6) was reacted with trimethyl tin azide to give trimethyl tin tetrazole compound, which was hydrolysed to give tetrazole compound. The tetrazole compound was reacted with trityl chloride to give trityl Losartan of the formula (7). The reaction scheme of the process is shown in the Scheme 4.

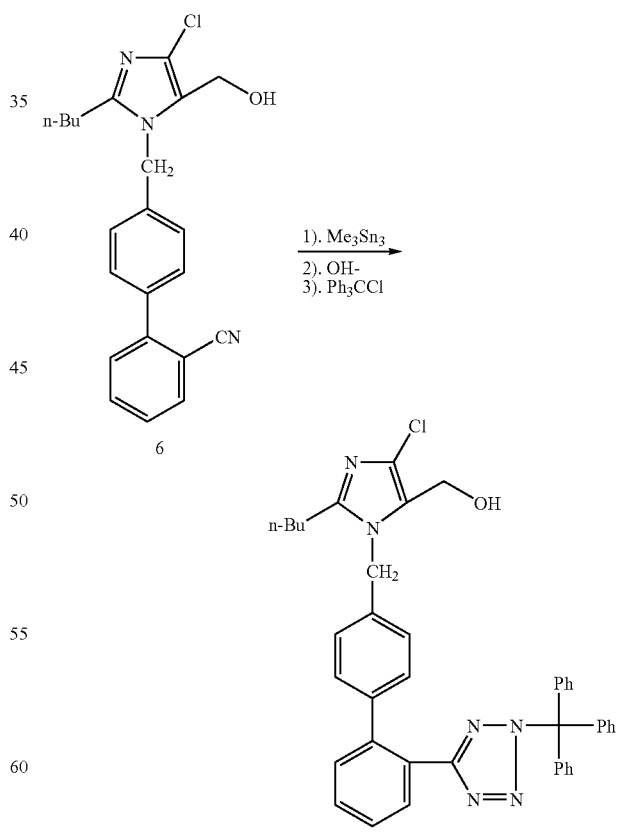

In the same paper the compound of the formula (7) is prepared by reacting 2-butyl-4-chloro-5-formyl imidazole of the formula (4) with N-(Triphenylmethyl)-5-[4'-(bromomethyl)biphenyl-2-yl]tetrazole of the formula (11) in the presence of base and the resulting aldehyde is reduced with Sodium borohydride to give Trityl Losartan of the formula (7).

The reaction scheme of the process is shown in Scheme 5.

Scheme 5

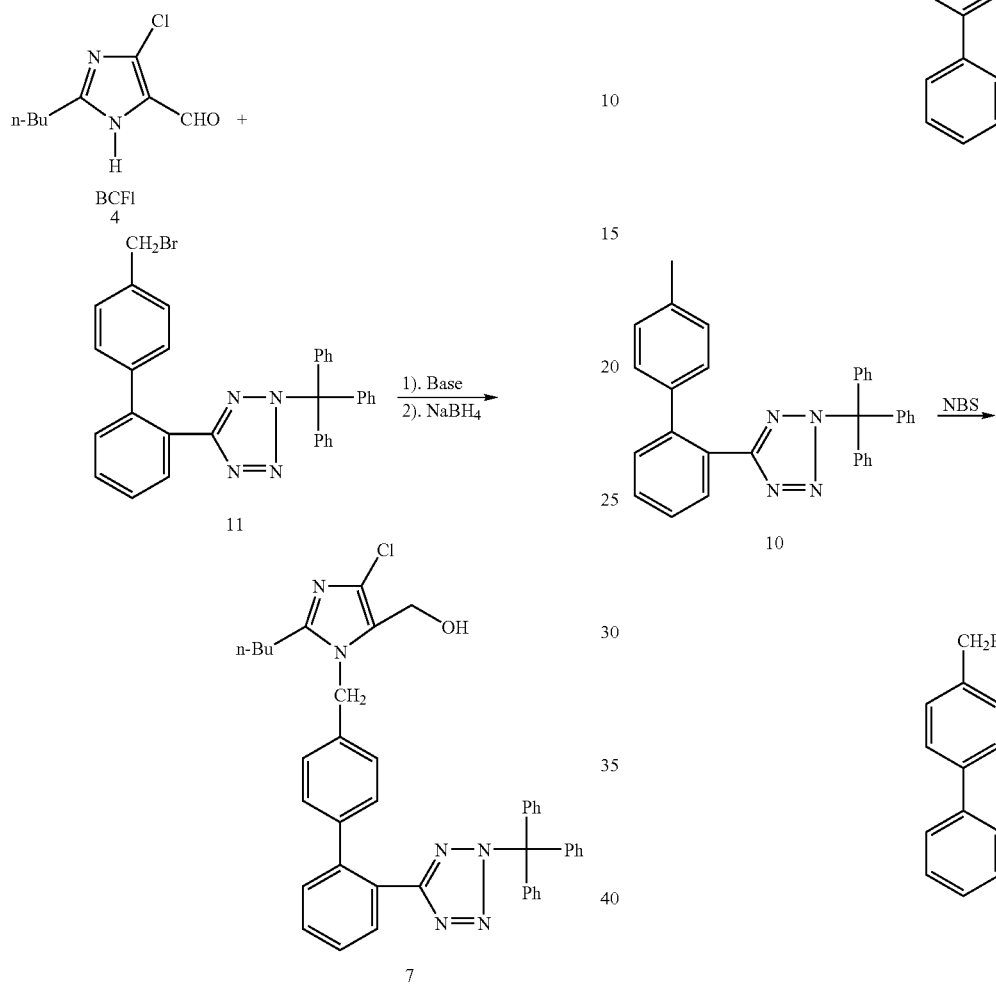

The compound of the formula (11) is prepared using tri alkyl tin azide. Ortho tolyl benzonitrile (OTBN of the formula (8) is reacted with trialkyl tin azide followed by hydrolysis to give tetrazole derivative of the formula (9). The tetrazole derivative is reacted with trityl chloride to give trityl tetrazole derivative of the formula (10), which on radical bromination gives compound of the formula (11). The reaction sequence is given in the Scheme 6.

Scheme 6

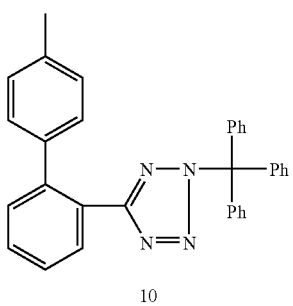

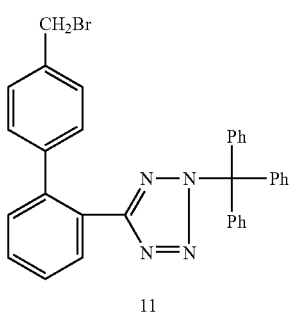

Merck/Dupont in their patent EP 0253310, dated 20 Jan. 1988 published a simple route to prepare Losartan but it involves column chromatography for the purification of Cyano alcohol of the formula (6), from its regioisomer impurity of the formula (12)

The tetrazole formation from cyano alcohol of the formula (6) takes 13 days for completion. This reaction of the process is shown in the scheme 7.

Scheme 7

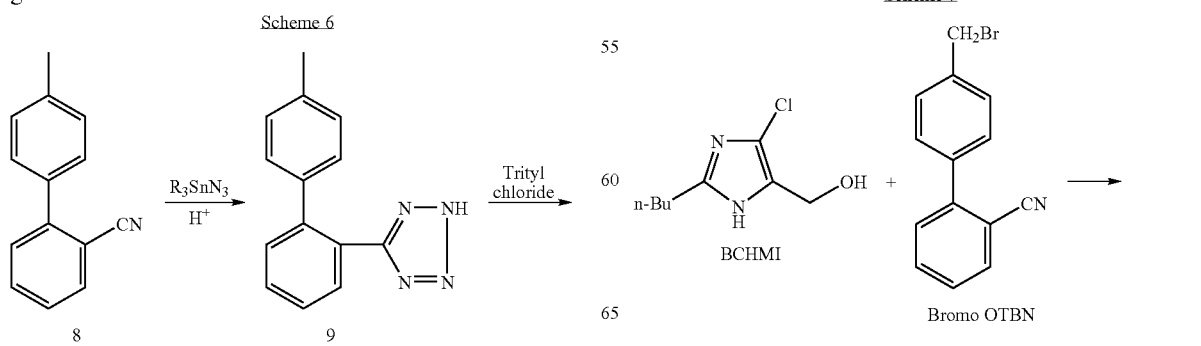

-continued

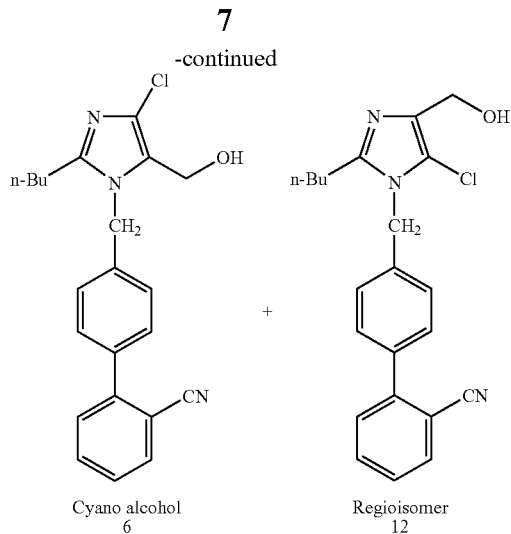

Cyano alcohol
6

Regioisomer
12

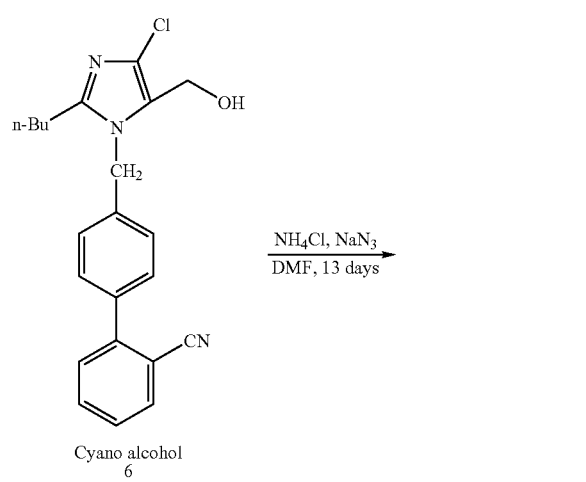

4,820,843 dated Apr. 11, 1989, in Example 7, they prepared trityl Losartan of the formula (7) in 21% yield All the processes described above uses metal asides for the preparation of Tetrazole derivative. Metals such as aluminium (in diethyl aluminium azide) and tin compounds like tri-n-octyl tin azide and trialkyl tin azides are environmentally hazardous chemicals and their disposals are not only cause always problems but also need special methods such as totally recovering the metal from the effluents, which needs ion-exchage chromatography (an additional investment) or complexation techniques.

Hence there is a continuous urge to develop environment friendly and an economical process for the drug Losartan of the formula 1.

OBJECTIVES OF THE INVENTION

Accordingly, the main objective of the present invention is to provide an improved process for the preparation of Losartan of the formula I overcoming the drawbacks of the hitherto known processes.

Another objective of the present invention is to provide an improved process for the preparation of Losartan of the formula I which is simple and environmentally friendly Still another objective of the present invention is to provide an improved process for the preparation of Losartan of the formula I in short reaction times and without employing metal azides and the like.

Yet another objective of the present invention is to provide an improved process for the preparation of Losartan of the formula I in short number of steps to make it economical and with good yields. (>75%)

The above objectives of present invention have been achieved by avoiding metal azide usage in the preparation of tetrazole derivatives such as Losartan of the formula 1 Such a process is not reported in the literature and makes the process novel

SUMMARY OF THE INVENTION

The reaction scheme of the process of preparing Losartan of the formula I according to the present invention is shown in Scheme 8.

Scheme 8

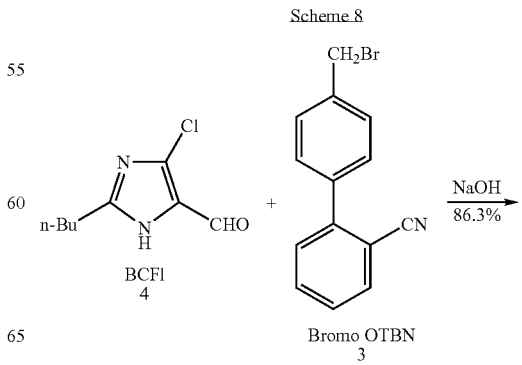

Even though Merck-Dupont had number of patents and publications being innovator of the drug, their processes to reach the final drug molecule is lengthy and yields are moderate at some stages. For example in patent U.S. Pat. No.

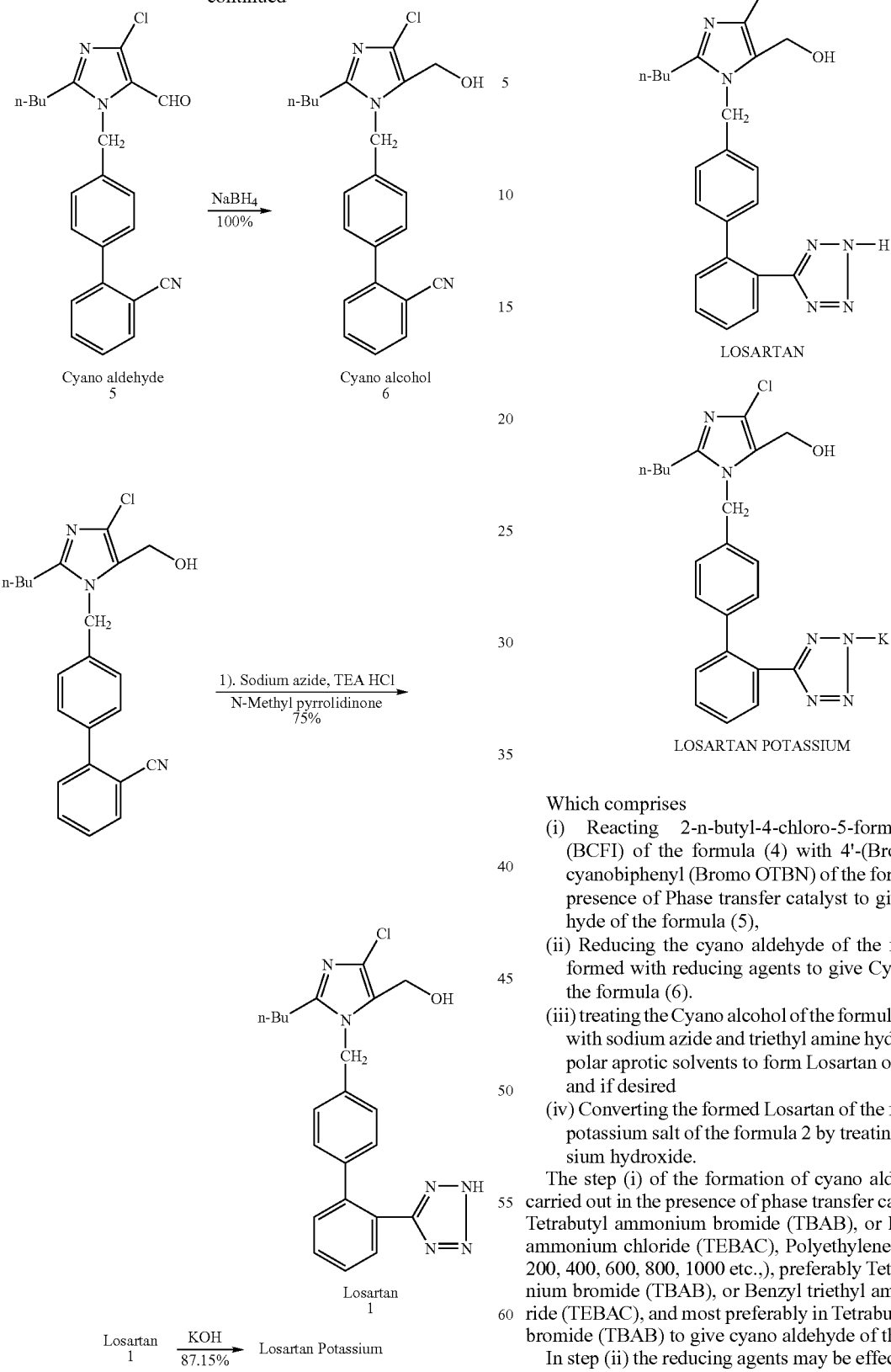

Accordingly, the present invention provides an improved process for the preparation of Losartan of the formula 1 or its potassium salt of the formula 2.

Which comprises
(i) Reacting 2-n-butyl-4-chloro-5-formyl imidazole (BCFI) of the formula (4) with 4'-(Bromomethyl)-2-cyanobiphenyl (Bromo OTBN) of the formula (3) in the presence of Phase transfer catalyst to give cyano aldehyde of the formula (5),
(ii) Reducing the cyano aldehyde of the formula (5) so formed with reducing agents to give Cyano alcohol of the formula (6).
(iii) treating the Cyano alcohol of the formula (6) so formed with sodium azide and triethyl amine hydrochloride in a polar aprotic solvents to form Losartan of the formula 1 and if desired
(iv) Converting the formed Losartan of the formula 1 to its potassium salt of the formula 2 by treating it with potassium hydroxide.

The step (i) of the formation of cyano aldehyde may be carried out in the presence of phase transfer catalysts such as Tetrabutyl ammonium bromide (TBAB), or Benzyl triethyl ammonium chloride (TEBAC), Polyethylene Glycol (PEG-200, 400, 600, 800, 1000 etc.,), preferably Tetrabutyl ammonium bromide (TBAB), or Benzyl triethyl ammonium chloride (TEBAC), and most preferably in Tetrabutyl ammonium bromide (TBAB) to give cyano aldehyde of the formula (5).

In step (ii) the reducing agents may be effected using such as Lithium Aluminium hydride, sodium borohydride, Potassium borohydride preferably low cost Sodium borohydride.

The step (iii) of the formation of tetrazole formation may be carried out in polar aprotic solvents such as DMF, DMSO, NMP (N-methylpyrrolidinone), DMI (dimethyl imidazolidinone) and Dimethyl acetamide, preferably N-methylpyrrolidinone and DMF and most preferably in N-methylpyrrolidinone. This step may also carried out in the presence of salts such as pyridine hydrochloride, Triethyl amine hydrochloride, Piperidine acetate, dialkyl amine hydrochloride, preferably in the presence of pyridine hydrochloride or Triethyl amine hydrochloride and most preferably in the presence of Triethyl amine hydrochloride.

The reaction temperature of step (iii) may be between 90-130° C. and preferably between 100-120° C. and most preferably between 100-110° C. and the reaction period may range between 20-40 hours, preferably 25-30 hours and most preferably between 28-30 hours.

The details of the invention are given in Examples given below which are provided by way of illustration only and therefore should not be construed to limit the scope of invention.

EXAMPLE-1

Preparation of Losartan Potassium

Step (I): Preparation of 2-n-butyl-4-chloro-1-[2'-(cyanobiphenyl-4-yl)methyl]-5-(hydroxymethyl)-imidazole of the formula (6)

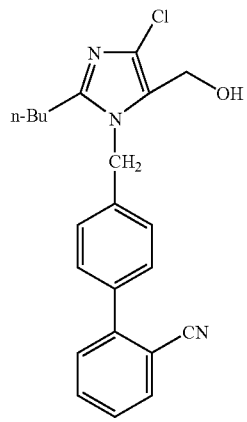

6

To a stirred solution of DM Water (360 ml), sodium hydroxide flakes (14.4 gm, 0.36 M) was added toluene (900 ML), Tetrabutyl ammonium bromide (TBAB) (7.2 gm), 4'-(Bromomethyl)-2-cyanobiphenyl (90 gm, 0.33 M) and 2-butyl-4-chloro-5-formyl imidazole (65 gm, 0.34 M) at room temperature (25-30° C.). The solution was stirred at room temperature for 28-30 hours. After TLC completed the reaction, the organic layer was separated and the aqueous layer was extracted with 200 ml of toluene. The combined organic layers were washed with 150 ml of 7% sodium hydroxide solution and then finally washed with 200 ml of water. Toluene layer was preceded further without isolation of cyano aldehyde of the formula 5.

To the stirred solution of toluene with compound of the formula 5 (approximately 1200 ml) was added sodium borohydride (12.6 gm, 0.33 M) at room temperature (25-30° C.). The reaction temperature was raised to 40-45° C. and methanol was added at 40-45° C. over a period of 1 hour. After the methanol addition, maintained for 3 hours at 40-45° C. After TLC showed the conversion >99%, it was cooled to 25-30° C. and 1100 ml of water was added. Further cooled to 10-15° C. The cooled solution was filtered and washed with water to get 2-n-butyl-4-chloro-1-[2'-(cyanobiphenyl-4-yl)methyl]-5-(hydroxymethyl)-imidazole of the formula of the formula 6 (Yield 86%)

Melting point 154-156° C.
HPLC Purity. >98%
IR. ν max (KBR): 3275.27 (—CH$_2$OH), 2221 (—CN),
$^1$H NMR (CDCl3) δ, 0.88 (t, 3H), 1.35 (sext, 2H), 1.69 (quint, 2H), 2.6 (t, 2H), 4.51 (s, 2H), 5.30 (s, 2H), 7.11-7.77 (m, 8H).
$^{13}$C NMR (CDCl3) δ, 13.64, 22.30, 26.63, 29.60, 47.11, 52.85, 111.05, 118.47, 124.99, 126.2, 127.0, 127.7, 129.29, 129.9, 132.8, 133.7, 136.72, 137.65, 144.52, 148.5
MS (m/z)=380.2 (M+1).

Step-II: Preparation of 2-n-butyl-4-chloro-5-hydroxymethyl-1-[(2'-(1H-tetrazole-5-yl)biphenyl-4-yl)methyl]imidazole [Losartan] of the formula (1)

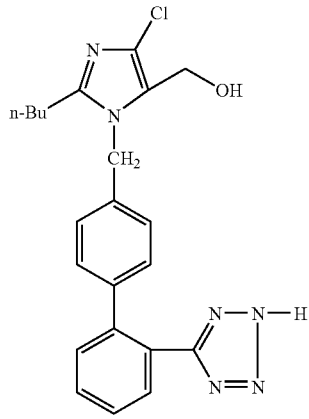

1

To a stirred solution of 2-n-butyl-4-chloro-1-[2'-cyanobiphenyl-4-yl)methyl]-5-(hydroxymethyl) imidazole (105 gm, 0.276 M) prepared by the process described in step I in 210 ml of N-methylpyrrolidinone at room temperature was added Triethyl amine hydrochloride (75 gm, 0.545 M) and sodium azide (35 gm, 0.54 M) at room temperature (25-30° C.). The reaction temperature was raised to 103-105° C. and maintained for 28-30 hours. TLC showed the absence of starting material.

The reaction mixture was cooled to 45-50° C. and charged 300 ml of toluene, 800 ml of water with stirring. The organic layer was separated and aqueous layer was washed with 250 ml of toluene. The aqueous layer was treated with 10 grams of activated carbon and filter through celite. Aqueous layer PH was adjusted to 4.3-4.5 with acetic acid (70-75 ml) and was stirred for 8 hours at 25-30° C. The aqueous solution was filtered and washed with water to get the Losartan of the formula (1). (Yield: >75%).

Melting point 180.5-181.2
HPLC Purity: >98%
IR. ν max (KBR): 3376.27, 1579.77, 1468.86, 762.88, 556.4
$^1$H NMR (CDCl3) δ, 0.87 (t, 3H), 1.31 (sext, 2H), 1.54 (quint, 2H), 2.57 (t, 2H), 4.45 (s, 2H), 5.30 (s, 2H), 7.01-7.68 (m, 8H).
$^{13}$C NMR (CDCl3) δ, 14.07, 23.24, 27.40, 30.92, 126.71, 126.86, 127.35, 128.21, 130, 130.8, 131, 131.19, 131.81, 136.09, 142.21, 149.97, 162.72
MS (m/z)=423.5 (M+1).

Step-III: Preparation of 2-n-butyl-4-chloro-5-hydroxymethyl-1-[2'-(1H-tetrazole-5-yl)biphenyl-4-yl)methyl]imidazole: Potassium salt of Losartan of the formula (2).

To a stirred solution of 2-n-butyl-4-chloro-5-hydroxymethyl-1-[(2'-(1H-tetrazole-5-yl)biphenyl-4-yl)methyl]imidazole (Losartan of the formula (I)) obtained in step II (50 gm, 0.118 M) in 250 ml of methanol was added potassium hydroxide powder [7.6 gm (86%), 0.118 M] at room temperature (25-30° C.). The reaction temperature was raised to reflux (60-63° C.) and maintained for 4-5 hours at 60-63° C. The reaction mixture was cooled to 35-40° C. This was filtered through celite and the clarified solution was concentrated to remove most of methanol at 45-50° C. under reduced pressure. 100 ml of Methyl ethyl ketone was added and distillation continued to distill most of the methanol/methyl ethyl ketone mixture. Residue was diluted with 200 ml of Acetone and contents cooled to 5-10° C. for 30 minutes and product filtered and washed with 50 ml of acetone. Product was dried under reduced pressure to yield 47.5 grams. (87.15% of theory) of Losartan Potassium of the formula (2).

HPLC Purity: 99.81%.

IR. ν max (KBR): 3201.01, 1580.73, 1460.18, 764.81, 540.09

$^1$H NMR (MeOD) δ, 0.87 (t, 3H), 1.33 (sext, 2H), 1.53 (quint, 2H), 2.56 (t, 2H), 4.43 (s, 2H), 5.24 (s, 2H), 6.89-7.53 (m, 8H).

$^{13}$C NMR (MeOD) δ, 14.07, 23.24, 27.40, 30.92, 126.71, 126.86, 127.35, 128.21, 130, 130.8, 131, 131.19, 131.81, 136.09, 142.21, 149.97, 162.72

MS (m/z)=423.3 (M+1).

EXAMPLE-2

Preparation of Losartan Potassium

Step (I): Preparation of 2-n-butyl-4-chloro-1-[2'-(cyanobiphenyl-4-yl)methyl]-5-(hydroxymethyl)-imidazole of the formula 6

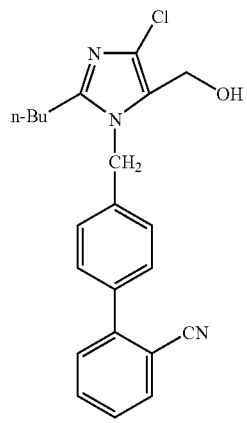

To a stirred solution of DM Water (360 ml), sodium hydroxide flakes (14.4 gm, 0.36 M) was added toluene (900 ML), Benzyl triethyl ammonium chloride (TEBAC) (72 gm), 4'-(Bromomethyl)-2-cyanobiphenyl (90 gm, 0.33 M) and 2-butyl-4-chloro-5-formyl imidazole (65 gm, 0.34 M) at room temperature (25-30° C.). The solution was stirred at room temperature for 28-30 hours. After TLC completes the reaction, the organic layer is separated and the aqueous layer is extracted with 200 ml of toluene. The combined organic layers were washed with 150 ml of 7% sodium hydroxide solution and then finally washed with 200 ml of water. Toluene layer is proceed further without isolation of cyano aldehyde of the formula 5.

To the stirred solution of toluene with compound of the formula 5 (approximately 1200 ml) was added sodium borohydride (12.6 gm, 0.33 M) at room temperature (25-30° C.). The reaction temperature was raised to 40-45° C. and methanol was added at 40-45° C. over a period of 1 hour. After the methanol addition, maintained for 3 hours at 40-45° C. After TLC showed the conversion >99%, it was cooled to 25-30° C. and 1100 ml of water was added. Further cooled to 10-15° C. The cooled solution was filtered and washed with water to get the cyano alcohol of the formula (6). (Yield 86%)

Melting point: 154-156° C.

HPLC Purity: >98%

IR. ν max (KBR): 3275.27 (—CH$_2$OH), 2221 (—CN), $^1$H NMR (CDCl3) δ, 0.88 (t, 3H), 1.35 (sext, 2H), 1.69 (quint, 2H), 2.6 (t, 2H), 4.51 (s, 2H), 5.30 (s, 2H), 7.11-7.77 (m, 8H).

$^{13}$C NMR (CDCl3) δ, 13.64, 22.30, 26.63, 29.60, 47.11, 52.85, 111.05, 118.47, 124.99, 126.2, 127.0, 127.7, 129.29, 129.9, 132.8, 133.7, 136.72, 137.65, 144.52, 148.5 MS (m/z)= 380.2 (M+1).

Step-II: Preparation of 2-n-butyl-4-chloro-5-hydroxymethyl-1-[(2'-(1H-tetrazole-5-yl)biphenyl-4-yl)methyl]imidazole [Losartan] of the formula I

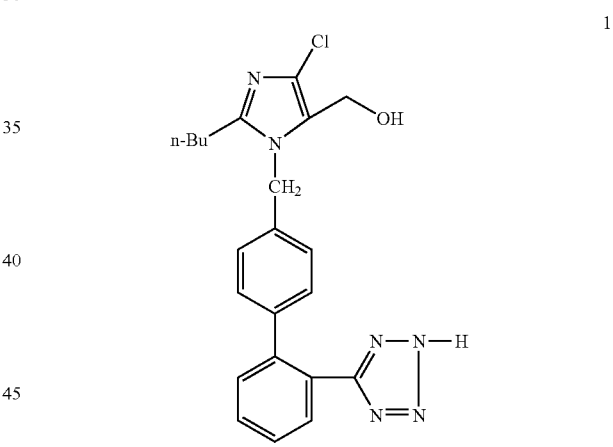

To a stirred solution of 2-n-butyl-4-chloro-142'-cyanobiphenyl-4-yl)methyl)-5-(hydroxymethyl) imidazole (105 gm, 0.276 M) prepared by the process described in step I in 210 ml of N-methylpyrrolidinone at room temperature was added TEA HCl (75 gm, 0.545 M) and sodium azide (35 gm, 0.54 M) at room temperature (25-30° C.). The reaction temperature was raised to 103-105° C. and maintained for 28-30 hours. TLC showed the absence of starting material.

The reaction mixture was cooled to 45-50° C. and charge 300 ml of toluene, 800 ml of water with stirring. The organic layer was separated and aqueous layer was washed with 250 ml of toluene. The aqueous layer is treated with 10 grams of activated carbon and filter through celite. Aqueous layer PH was adjusted to 4.3-4.5 with acetic acid (70-75 ml) and was stirred for 8 hours at 25-30° C. The aqueous solution was filtered and washed with water to get Losartan of the formula 1. (Yield: >75%).

Melting point: 180.5-181.2

HPLC Purity: >98%

IR. ν max (KBR): 3376.27, 1579.77, 1468.86, 762.88, 556.4

¹H NMR (CDCl3) δ, 0.87 (t, 3H), 1.31 (sext, 2H), 1.54 (quint, 2H), 2.57 (t, 2H), 4.45 (s, 2H), 5.30 (s, 2H), 7.01-7.68 (m, 8H).

¹³C NMR (CDCl3) δ, 14.07, 23.24, 27.40, 30.92, 126.71, 126.86, 127.35, 128.21, 130, 130.8, 131, 131.19, 131.81, 136.09, 142.21, 149.97, 162.72

MS (m/z)=423.5 (M+1).

Step-III: Preparation of 2-n-butyl-4-chloro-5-hydroxymethyl-1-[2'-(1H-tetrazole-5-yl)biphenyl-4-yl) methyl]imidazole: Potassium salt of Losartan formula (2).

To a stirred solution of 2-n-butyl-4-chloro-5-hydroxymethyl-1-[(2'-(1H-tetrazole-5-yl)biphenyl-4-yl)methyl]imidazole (Losartan I) obtained by the process described in step II (50 gm, 0.118 M) in 250 ml of methanol was added potassium hydroxide powder [7.6 gm (86%), 0.118 M] at room temperature (25-30° C.). The reaction temperature is raised to reflux (60-63° C.) and maintained for 4-5 hours at 60-63° C. The reaction mixture was cooled to 35-40° C. This was filtered through celite and the clarified solution was concentrated to remove most of methanol at 45-50° C. under reduced pressure. 100 ml of Methyl ethyl ketone was added and distillation continued to distill most of the methanol/methyl ethyl ketone mixture. Residue was diluted with 200 ml of Acetone and contents cooled to 5-10° C. for 30 minutes and product filtered and washed with 50 ml of acetone. Product was dried under reduced pressure to yield 47.5 grams. (87.15% of theory) Losartan Potassium of the formula (2).

HPLC Purity: 99.82%.

IR. ν max (KBR): 3201.01, 1580.73, 1460.18, 764.81, 540.09

¹H NMR (MeOD) δ, 0.87 (t, 3H), 1.33 (sext, 2H), 1.53 (quint, 2H), 2.56 (t, 2H), 4.43 (s, 2H), 5.24 (s, 2H), 6.89-7.53 (m, 8H).

¹³C NMR (MeOD) δ, 14.07, 23.24, 27.40, 30.92, 126.71, 126.86, 127.35, 128.21, 130, 130.8, 131, 131.19, 131.81, 136.09, 142.21, 149.97, 162.72

MS (m/z)=423.3 (M+1).

ADVANTAGES OF THE INVENTION

1. The process does not use reagents such as heavy metal azides, tri-n-butyl tin azide, and tri-n-Octyl tin azide, therefore environmentally safe.
2. Consequently there is no disposal problems
3. The process is easy to perform and in less number of steps and hence economical.
4. The yield of Losartan produced is enhanced (>75%) and the purity of (>99%)
5. The process is commercially applicable.

We claim:

1. A process for the preparation of Losartan having the formula:

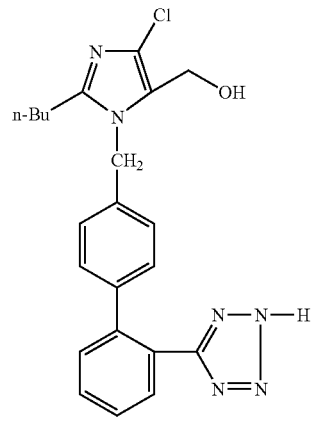

the process comprising:

(i) reacting 2-n-butyl-4-chloro-5-formyl imidazole of the formula:

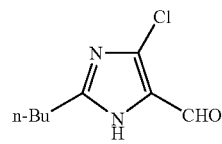

with 4'-(Bromomethyl)-2-cyanobiphenyl of the formula:

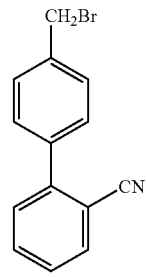

in the presence of a phase transfer catalyst to produce a cyano aldehyde of the formula

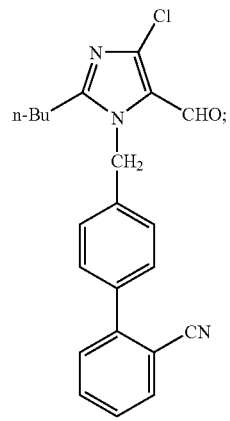

(ii) reducing the formed cyano aldehyde with a reducing agent to produce a cyano alcohol of the formula

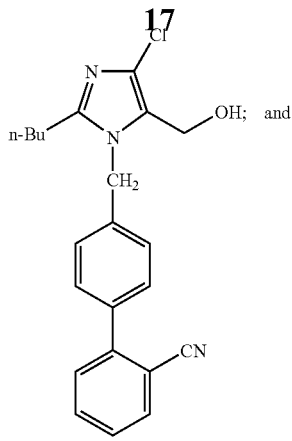

(iii) treating the formed cyano alcohol with sodium azide and triethyl amine hydrochloride in a polar aprotic solvent to produce Losartan.

2. The process as claimed in claim 1 wherein the phase transfer catalyst is selected from the group consisting of: tetrabutyl ammonium bromide, benzyl triethyl ammonium chloride, and polyethylene glycol.

3. The process as claimed in claim 1 wherein the reducing agent is selected from the group consisting of: lithium aluminum hydride, sodium borohydride, and potassium borohydride.

4. The process as claimed in claim 1 wherein the polar aprotic solvent is selected from the group consisting of: dimethylformamide, dimethyl sulfoxide, NMP (N-methyl pyrrolidinone), DMI (dimethyl imidazolidinone) and Dimethyl acetamide.

5. The process as claimed in claim 1 wherein the treatment of the formed cyano alcohol is carried out in the presence of at least one salt selected from the group consisting of: pyridine hydrochloride, triethyl amine hydrochloride, piperidine acetate, and dialkyl amine hydrochloride.

6. The process as claimed in claim 1 wherein the treatment of the formed cyano alcohol is carried out at a temperature between 90-130° C.

7. The process as claimed in claim 1 wherein the treatment of the cyano alcohol is carried out for a time period in the range between 20-40 hours.

8. The process as claimed in claim 1 wherein the polar aprotic solvent is N-methyl pyrrolidinone.

9. The process as claimed in claim 1 wherein the polar aprotic solvent is dimethylformamide.

10. The process as claimed in claim 1 wherein the polar aprotic solvent is N-methyl pyrrolidinone.

11. The process as claimed in claim 1 wherein the treatment of the formed cyano alcohol is carried out in the presence of pyridine hydrochloride.

12. The process as claimed in claim 1 wherein the treatment of the formed cyano alcohol is carried out in the presence of triethyl amine hydrochloride.

13. The process as claimed in claim 1 wherein the treatment of the formed cyano alcohol is carried out in the presence of triethyl amine hydrochloride.

14. The process as claimed in claim 1 wherein the treatment of the formed cyano alcohol is carried out at a temperature between 100-120° C.

15. The process as claimed in claim 1 wherein the treatment of the formed cyano alcohol is carried out at a temperature between 100-110° C.

16. The process as claimed in claim 1 wherein the treatment of the cyano alcohol is carried out for a time period in the range between 25-30 hours.

17. The process as claimed in claim 1 wherein the treatment of the cyano alcohol is carried out for a time period in the range between 28-30 hours.

18. The process as claimed in claim 1 further comprising the step of forming a potassium salt of Losartan by treating the formed Losartan with potassium hydroxide, the potassium salt of the Losartan having the formula:

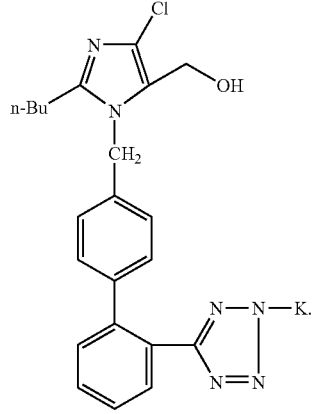

* * * * *